(12) United States Patent
Nakazato et al.

(10) Patent No.: US 6,281,355 B1
(45) Date of Patent: Aug. 28, 2001

(54) NITROGEN-CONTAINING TETRACYCLIC COMPOUNDS

(75) Inventors: Atsuro Nakazato; Taketoshi Okubo; Toshihito Kumagai; Shigeyuki Chaki; Kazuyuki Tomisawa, all of Tokyo; Masashi Nagamine, Nara; Makoto Gotoh, Osaka; Kuniaki Kondoh, Osaka; Masanori Yoshida, Osaka, all of (JP)

(73) Assignees: Taisho Pharmaceutical Co., Ltd.; Nihon Nohyaku Co., Ltd., both of (JP)

( * ) Notice: Subject to any disclaimer, the term of this patent is extended or adjusted under 35 U.S.C. 154(b) by 0 days.

(21) Appl. No.: 09/555,570
(22) PCT Filed: Dec. 3, 1998
(86) PCT No.: PCT/JP98/05452
  § 371 Date: Jun. 1, 2000
  § 102(e) Date: Jun. 1, 2000
(87) PCT Pub. No.: WO99/28298
  PCT Pub. Date: Jun. 10, 1999

(30) Foreign Application Priority Data

Dec. 3, 1997 (JP) .................................................. 9-332538

(51) Int. Cl.$^7$ ...................... A61K 31/403; A61K 31/437; C07D 209/80; C07D 471/04; C07D 495/04
(52) U.S. Cl. .......................... 544/14; 544/245; 544/247; 548/301.7; 548/420; 514/224.5; 514/257; 514/387; 514/410; 549/24
(58) Field of Search .................... 544/245, 247, 544/14; 548/301.7, 420; 514/224.5, 257, 387, 410

(56) References Cited

U.S. PATENT DOCUMENTS 3,658,456   4/1972   Hertel .......................... 8/44
5,206,382   4/1993   Costa et al. ................... 548/494

FOREIGN PATENT DOCUMENTS

B-46-37191   11/1971   (JP) .
6-501030   2/1994   (JP) .

OTHER PUBLICATIONS

Papadopoulos, Vassilios et al., "Pregrenolone biosynthesis in C6–2B glioma cell mitochondria: regulation by a mitochondrial diazepam binding inhibitor receptor", Proc. Natl. Acad. Sci. U.S.A., 89 (11), (1992), p. 5113–17.

*Primary Examiner*—Mukund J. Shah
*Assistant Examiner*—Venkataraman Balasubramanian
(74) *Attorney, Agent, or Firm*—Lorusso & Loud

(57) ABSTRACT

A nitrogen-containing tetracyclic compound represented by the formula:

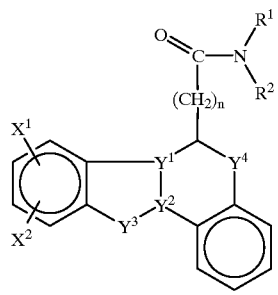

wherein $Y^1$—$Y^2$—$Y^3$ is N—C=N or a group represented by the formula: C=C—NR$^3$ (wherein R$^3$ is a hydrogen atom, a $C_{1-5}$ alkyl group or a nitrogen-containing $C_{2-10}$ alkyl group), $Y^4$ is S, SO, SO$_2$, CH$_2$ or a group represented by the formula: NR$^4$ (wherein R$^4$ is a $C_{1-5}$ alkanoyl group or a $C_{1-5}$ alkyl group), R$^1$ and R$^2$ are the same or different, and are each a hydrogen atom, a $C_{1-10}$ alkyl group, a $C_{3-15}$ alkoxyalkyl group or a $C_{3-15}$ alkylaminoalkyl group, or R$^1$ and R$^2$ taken together with the nitrogen atom to which they are attached form a cyclic amino group, $X^1$ and $X^2$ are the same or different, and are each a hydrogen atom, a $C_{1-5}$ alkyl group, a $C_{1-5}$ alkoxy group or a halogen atom, and n is 0, 1 or 2; or a pharmaceutically acceptable salt thereof.

1 Claim, No Drawings

NITROGEN-CONTAINING TETRACYCLIC COMPOUNDS

TECHNICAL FIELD

The present invention relates to compounds having a high affinity for mitochondrial diazepam binding inhibitor receptor (MDR).

BACKGROUND ART

Benzodiazepine (BZ) receptors which are an acting site of anti-anxiety drugs are classified into 2 subtypes of central benzodiazepine receptor (CBR) located on $GABA_A$ receptor/chloride channel complex and MDR located on the central nervous system (glial cells) or adrenal glands (Clin. Neuropharmacol., 16, 401–417 (1993)). Recently, CBR agonists of which representative is diazepam are widely used as anti-anxiety drugs. However, since CBR agonists act directly on $GABA_A$ receptor/chloride channel complex, they cause an anti-anxiety action together with side-effects such as excessive sedation or psychic dependence. On the other hand, since MDR agonists act indirectly on $GABA_A$ receptor/chloride channel complex via synthesis of neurosteroids such as endogenous neuroactive steroids (endogenous anti-anxiety substances), they cause an anti-anxiety action, but do not cause side-effects such as psychic dependency or excessive sedation (J. Pharmacol. Exp. Ther., 267, 462–471, 1993; ibid., 265, 649–656, 1993).

Accordingly, there is a need of the development of therapeutic agents for diseases (obsessive disorders, panic disorders) on which the previous BZs do not have a satisfactorily therapeutic effect, and development of MDR agonists as anti-anxiety drugs which alleviate the side-effects as recognized in the previous BZs.

Furthermore, the compounds which act on MDR, in view of acting on $GABA_A$ receptors, have a possibility of use as therapeutical agents of sleeping disorders, epilepsy, dyskinesia accompanied by muscle rigidity, feeding disorders, circulation disorders, recognition and learning disability or drug dependence (Progress in Neurobiology, 38, 379–395, 1992, ibid., 49, 73–97, 1996; J. Neurochem., 58, 1589–1601; Neuropharmacol., 30, 1435–1440, 1991). In addition, these compounds, in view of the physiological functions of MDR, have a possibility of use as therapeutic agents of cancer (Biochimica et Biophysica Acta, 1241, 453–470, 1995), lipid metabolism abnormality (Eur. J. Pharmacol., 294, 601–607, 1995), schizophrenia (Neuropharmacology, 35, 1075–1079, 1996), cerebral infarction (J. Neurosci., 15, 5263–5274, 1995), AIDS (Abstracts of the fifth international conference on AIDS, p. 458, 1989), Alzheimer's disease (Alzheimer Dis. Assoc. Disotd., 2, 331–336, 1988) or Huntington chorea (Brain Res., 248, 396–401, 1982).

Among the compounds having affinity for MDR, there are indole compounds disclosed in Japanese Translation of PCT publication (Kohyo) No.6-501030.

DISCLOSURE OF THE INVENTION

As a result of extensive researches about compounds having a high affinity for MDR, the present inventors have found that the specific nitrogen-containing tetracyclic compounds meet the above object, thus the present invention has been accomplished. As stated above, while the indole compounds having an affinity for MDR are known, there are not reported nitrogen-containing tetracyclic compounds which have an affinity for MDR.

The present invention is directed to a nitrogen-containing tetracyclic compound represented by Formula [I]:

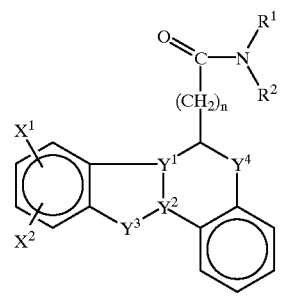

wherein $Y^1$—$Y^2$—$Y^3$ is N—C=N or a group represented by the formula: C=C—$NR^3$ (wherein $R^3$ is a hydrogen atom, a $C_{1-5}$ alkyl group or a nitrogen-containing $C_{2-10}$ alkyl group), $Y^4$ is S, SO, $SO_2$, $CH_2$ or a group represented by the formula: $NR^4$ (wherein $R^4$ is a $C_{1-5}$ alkanoyl group or a $C_{1-5}$ alkyl group), $R^1$ and $R^2$ are the same or different, and are each a hydrogen atom, a $C_{1-10}$ alkyl group, a $C_{3-15}$ alkoxyalkyl group or a $C_{3-15}$ alkylaminoalkyl group, or $R^1$ and $R^2$ taken together with the nitrogen atom to which they are attached form a cyclic amino group, $X^1$ and $X^2$ are the same or different, and are each a hydrogen atom, a $C_{1-5}$ alkyl group, a $C_{1-5}$ alkoxy group or a halogen atom, and n is 0, 1 or 2; or a pharmaceutically acceptable salt thereof.

In the present invention, the $C_{1-5}$ alkyl group for $R^3$, $R^4$, $X^1$ and $X^2$ refers to a straight, branched or cyclic alkyl group, and examples thereof are a methyl group, an ethyl group, a propyl group, an isopropyl group, a butyl group, an isobutyl group, a cyclopropylmethyl group, a pentyl group and an isopentyl group. Examples of the nitrogen-containing $C_{2-10}$ alkyl group for $R^3$ are a methylaminopropyl group, a dimethylaminoethyl group, a pyrrolidinoethyl group and a 4-methylpiperazinoethyl group. Examples of the $C_{1-5}$ alkanoyl group for $R^4$ are a formyl group, an acetyl group and a propionyl group. The $C_{1-10}$ alkyl group for $R^1$ and $R^2$ refers to a straight, branched or cyclic alkyl group, and examples thereof are a methyl group, an ethyl group, a propyl group, an isopropyl group, a cyclopropyl group, a butyl group, an isobutyl group, a cyclobutyl group, a cyclopropylmethyl group, a pentyl group, an isopentyl group, a cyclopentyl group, a cyclobutylmethyl group, a 1-ethylpropyl group, a hexyl group, an isohexyl group, a cyclohexyl group, a cyclopentylmethyl group, a 1-ethylbutyl group, a heptyl group, an isoheptyl group, a cyclohexylmethyl group, an octyl group, a nonyl group and a decyl group. The $C_{3-15}$ alkoxyalkyl group for $R^1$ and $R^2$ refers to a straight, branched or cyclic $C_{1-13}$ alkoxy-$C_{2-14}$ alkyl group, and examples thereof are a methoxyethyl group, a methoxypropyl group, a methoxybutyl group, an ethoxyethyl group, an ethoxypropyl group, an ethoxybutyl group, an ethoxypentyl group, an ethoxyhexyl group, an ethoxyheptyl group, a propoxyethyl group, a propoxypropyl group, a propoxybutyl group, an isopropoxyethyl group and a cyclopropylmethoxyethyl group. The $C_{3-15}$ alkylaminoalkyl group for $R^1$ and $R^2$ refers to a straight, branched or cyclic $C_{1-13}$ alkylamino-$C_{2-14}$ alkyl group, and examples thereof are a methylaminoethyl group, a dimethylaminoethyl group, a methylaminopropyl group, a dimethylaminopropyl group, a methylaminobutyl group, an ethylaminoethyl group, an ethylaminopropyl group, an ethylaminobutyl group, an ethylaminopentyl group, an ethylaminohexyl group, an ethylaminoheptyl group, an ethylaminooctyl group, a propylaminoethyl group, a propylaminopropyl group, a propylaminobutyl group, an isopropylaminoethyl group, a cyclopropylmethylaminoethyl group and a pyrrolidinoethyl group. Examples of the cyclic amino group which is formed by $R^1$, $R^2$ and the nitrogen atom to which they are attached are a pyrrolidino group, a piperidino group, a homopiperidino group, a morpholino group, a piperazino group, an N-methylpiperazino group and a 3,5-dimethylpiperazino group. The $C_{1-5}$ alkoxy group for $X^1$ and $X^2$ refers to a straight, branched or cyclic alkoxy group, and examples thereof are a methoxy group, an ethoxy group, a propoxy group, an isopropoxy group, a butoxy group, an isobutoxy group, a cyclopropylmethoxy group, a pentoxy group and an isopentoxy group. The halogen atom for $X^1$ and $X^2$ refers to a fluorine atom, a chlorine atom, a bromine atom or an iodine atom.

In addition, examples of the pharmaceutically acceptable salt in the present invention are salts with mineral acids such as sulfuric acid, hydrochloric acid or phosphoric acid, or salts with organic acids such as acetic acid, oxalic acid, lactic acid, tartaric acid, fumaric acid, maleic acid, methanesulfonic acid or benzenesulfonic acid.

The compound of Formula [I] can be prepared by the following general preparation methods 1 to 6. In the following reaction formulae, $Y^1$, $Y^2$, $Y^3$, $Y^4$, $R^1$, $R^2$, $X^1$, $X^2$ and n are as defined above, $R^5$ is a hydrogen atom or a $C_{1-5}$ alkyl group, $R^6$ is a $C_{1-5}$ alkyl group or a nitrogen-containing $C_{2-10}$ alkyl group, $R^7$ and $R^8$ are the same or different, and are each a $C_{1-5}$ alkyl group or a benzyl group, $X^3$ is a chlorine atom, a bromine atom or an iodine atom, $X^4$ is a fluorine atom, a chlorine atom, a bromine atom or an iodine atom, and Boc is a t-butoxycarbonyl group.

General Preparation Method 1

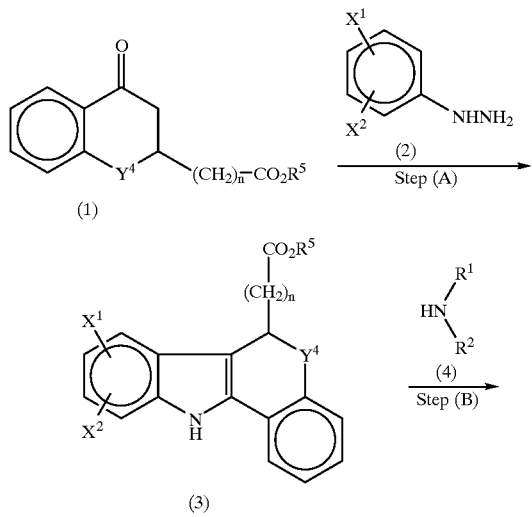

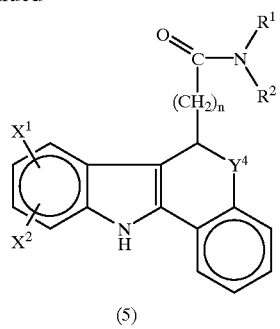

Step (A): A tetracyclic indole derivative (3) can be obtained using a ketocarboxylic acid derivative (1) and a phenylhydrazine derivative (2) according to a Fischer indole synthesis method. The tetracyclic indole derivative (3) wherein $R^5$ is a $C_{1-5}$ alkyl group can be hydrolyzed in the ester moiety with a conventional base or an acid to lead to a carboxylic acid derivative ($R^5$=H).

Step (B): The compound (5) of the present invention can be synthesized from the tetracyclic indole derivative (3) via the acid halide or mixed acid anhydride thereof.

The acid halide includes an acid chloride and an acid bromide, and for example, they can be obtained by reacting the tetracyclic indole derivative (3) ($R^5$=H) with a halogenating agent (e.g. thionyl chloride, thionyl bromide, oxalyl chloride, carbon tetrachloride-triphenylphosphine or carbon tetrabromide-triphenylphosphine) in an inert solvent. Examples of the above inert solvent are ethers (e.g. tetrahydrofuran), hydrocarbons (e.g. toluene or benzene), halogenide solvents (e.g. chloroform or dichloromethane), acetonitrile and N,N-dimethylformamide.

The mixed acid anhydride includes an anhydride of a carboxylic acid derivative (3) ($R^5$=H) with a carbonate ester or a carboxylic acid, and it can be obtained, for example, by reacting a halocarbonate (e.g. ethyl chlorocarbonate or isobutyl chlorocarbonate) or a carboxylic acid (e.g. acetic acid, propionic acid, benzoic acid or naphthoic acid) in the presence of an organic base (e.g. triethylamine, diisopropylethylamine, N-methylmorpholine or pyridine) or an inorganic base (e.g. sodium hydride) in an inert solvent. Examples of the inert solvent are ethers (e.g. tetrahydrofuran), hydrocarbons (e.g. toluene or benzene), halogenide solvents (e.g. chloroform or dichloromethane), acetonitrile and N,N-dimethylformamide.

The compound (5) of the present invention can be also obtained by the reaction of the tetracyclic indole derivative (3) together with a condensing agent and an amine (4) in an inert solvent.

The condensing agent refers to a conventional amidating reagent such as, diphenylphosphoryl azide, diethyl cyanophosphate, carbonyldiimidazole, N,N'-dicyclohexylcarbodiimide or N-ethyl-N'-dimethylaminopropylcarbodiimide hydrochloride. Examples of the inert solvent are ethers (e.g. 1,2-dimethoxyethane or tetrahydrofuran), hydrocarbons (e.g. toluene or benzene), halogenide solvents (e.g. chloroform or dichloromethane), acetonitrile and N,N-dimethylformamide. In this reaction, if necessary, N-hydroxysuccinimide, 1-hydroxybenzotriazole, 3-hydroxy-4-oxo-3,4-dihydro-1,2,3-benzotriazine, etc. can be added as an activating agent.

General Preparation Method 2

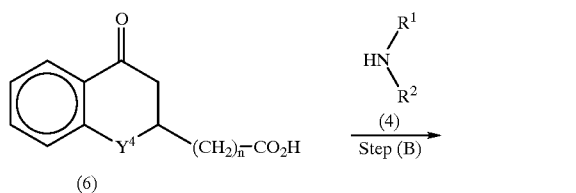

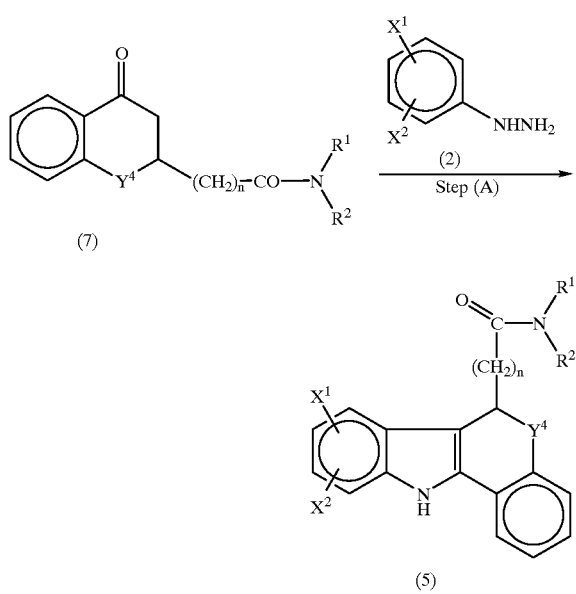

The compound (5) of the present invention can be also obtained by amidating a ketocarboxylic acid derivative (6) according to Step (B), and reacting the resulting ketoamide derivative (7) under the condition of the Fischer indole synthesis according to Step (A).

General Preparation Method 3

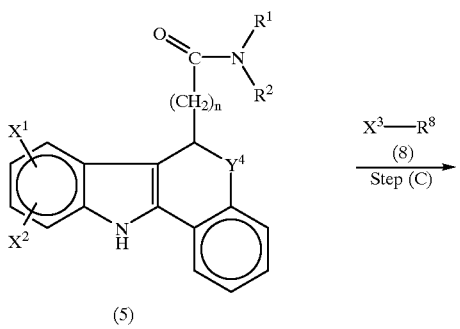

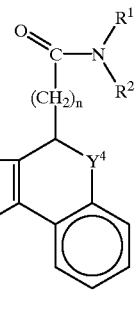

Step (C): The tetracyclic compound (5) can be reacted with a halide compound (8) together with a base in an inert solvent in the presence or absence of a phase transfer catalyst to give a compound (9) of the present invention.

Examples of the inert solvent are alcohols (e.g. methanol or ethanol), ethers (e.g. 1,2-dimethoxyethane or tetrahydrofuran), hydrocarbons (e.g. toluene or benzene), halogenide solvents (e.g. chloroform or dichloromethane), acetonitrile and N,N-dimethylformamide. Examples of the phase transfer catalyst are quaternary ammonium salts (e.g. benzyltriethyl ammonium bromide or tetrabutyl ammonium bromide) and crown ethers (e.g. 18-crown-6-ether). Examples of the base are inorganic bases (e.g. potassium carbonate, sodium hydroxide, sodium hydride or metallic sodium) and alcoholates (e.g. potassium t-butoxide or sodium ethoxide).

General Preparation Method 4

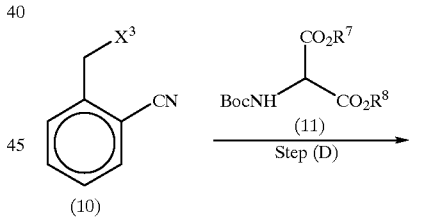

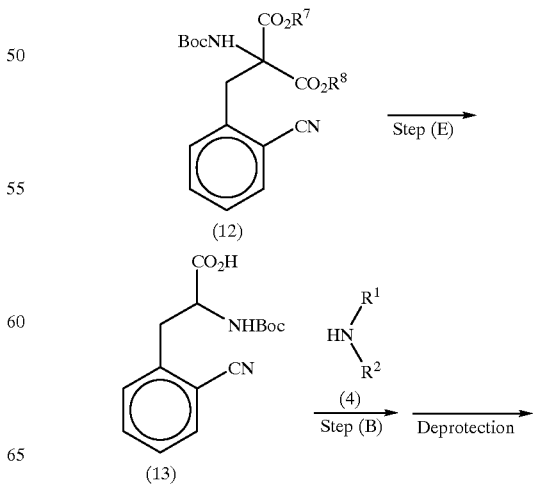

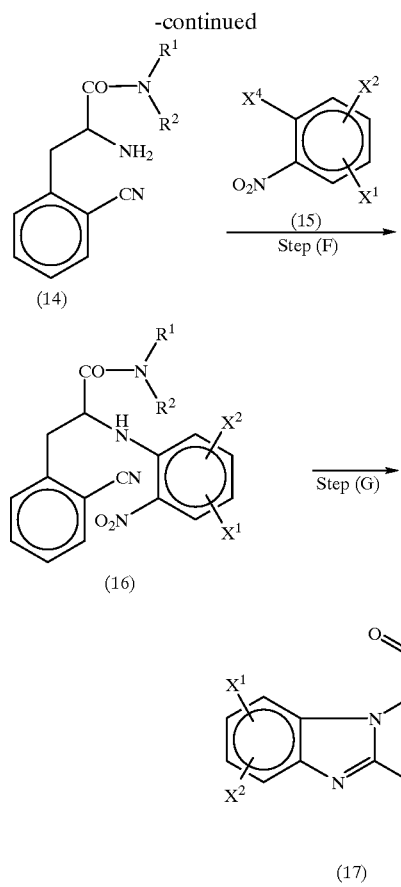

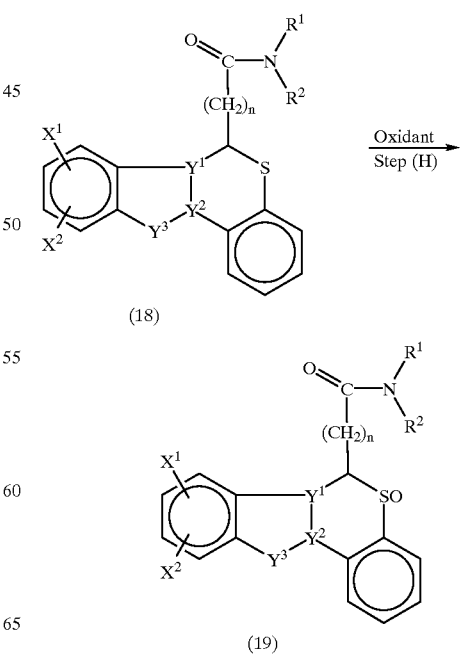

acid (e.g. hydrogen chloride, hydrochloric acid, hydrobromic acid or sulfuric acid) for deprotection to lead to an amide derivative (14).

Step (F): The amide derivative (14) is reacted with a nitrobenzene derivative (15) in the presence or absence of a base in an inert solvent to lead to an aniline derivative (16).

Examples of the base are inorganic bases (e.g. potassium carbonate, sodium carbonate, sodium hydroxide, sodium hydride or metallic sodium), alcoholates (e.g. potassium t-butoxide or sodium ethoxide) and organic bases (e.g. triethylamine, diisopropylethylamine or pyridine). Examples of the inert solvent are alcohols (e.g. methanol or ethanol), ethers (e.g. 1,2-dimethoxyethane, tetrahydrofuran or dioxane), hydrocarbons (e.g. toluene or benzene), halogenide solvents (e.g. chloroform or dichloromethane), acetonitrile and N,N-dimethylformamide.

Step (G): The nitro group of the aniline derivative (16) is reduced in an inert solvent and treated with an acid in an inert solvent to give a compound (17) of the present invention.

The reduction is carried out by hydrogenation using platinum dioxide, palladium or the like or by metal reduction using a metal (e.g. tin, iron or zinc) or a metal salt (e.g. stannous chloride) under acidic, neutral or basic conditions. Examples of the inert solvent are alcohols (e.g. methanol or ethanol), ethers (e.g. diethyl ether or tetrahydrofuran), hydrocarbons (e.g. toluene or benzene), halogenide solvents (e.g. dichloromethane or chloroform), acetonitrile N,N-dimethylformamide, organic carboxylic acids (e.g. acetic acid), water and a mixture thereof. The acid treatment in the inert solvent is to react using an acid (e.g. hydrogen chloride, hydrogen bromide, sulfuric acid or trifluoroacetic acid) in an alcohol alone (e.g. methanol or ethanol) or a mixture of the alcohol with an ether (e.g. diethyl ether, tetrahydrofuran), a hydrocarbon (e.g. toluene or benzene), a halogenide solvent (e.g. chloroform or dichloromethane) or N,N-dimethylformamide.

Step (D): A 2-cyanobenzyl halide (10) can be reacted with a 2-aminomalonic acid diester derivative (11) together with a base in an inert solvent in the presence or absence of a phase transfer catalyst to give a benzylmalonic acid derivative (12).

Examples of the inert solvent are alcohols (e.g. methanol or ethanol), ethers (e.g. 1,2-dimethoxyethane or tetrahydrofuran), hydrocarbons (e.g. toluene or benzene), halogenide solvents (e.g. chloroform or dichloromethane), acetonitrile and N,N-dimethylformamide. Examples of the phase transfer catalyst are quaternary ammonium salts (e.g. benzyltriethyl ammonium bromide or tetrabutyl ammonium bromide) and crown ethers (e.g. 18-crown-6-ether). The base includes inorganic bases (e.g., potassium carbonate, sodium hydroxide, sodium hydride or metallic sodium) or alcoholates (e.g. potassium t-butoxide or sodium ethoxide).

Step (E): The benzylmalonic acid derivative (12) can be hydrolyzed in the ester moiety with a base or an acid in an inert solvent, followed by decarbonation to give a phenylalanine derivative (13). Examples of the inert solvent are alcohols (e.g. methanol or ethanol), ketones (e.g. acetone), ethers (e.g. 1,2-dimethoxyethane or tetrahydrofuran), hydrocarbons (e.g. toluene or benzene), halogenide solvents (e.g. chloroform or dichloromethane), acetonitrile, N,N-dimethylformamide, water and a mixture thereof. Examples of the base are inorganic bases (e.g. potassium carbonate, sodium carbonate, potassium hydroxide or sodium hydroxide). Examples of the acid are hydrochloric acid, sulfuric acid and phosphoric acid.

In addition, the phenylalanine derivatives (13), after a reaction according to Step (B), is treated with an organic acid (e.g. trifluoroacetic acid or formic acid) or an inorganic General Preparation Method 5

-continued

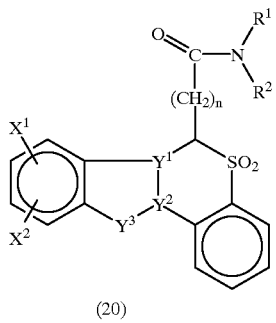

(20)

Step (H): A sulfur atom-containing tetracyclic compound (18) is treated with an oxidant in an inert solvent to give a racemic or optically active sulfoxide derivative (19) or sulfonic acid derivative (20).

Examples of the inert solvent are alcohols (e.g. methanol or ethanol), ethers (e.g. diethyl ether or tetrahydrofuran), hydrocarbons (e.g. toluene or benzene), halogenide solvents (e.g. dichloromethane or chloroform), acetonitrile, N,N-dimethylformamide, organic carboxylic acids (e.g. acetic acid), water and a mixture thereof. Examples of the oxidant are carboxylic peracids (e.g. m-chloroperbenzoic acid or peracetic acid) and inorganic peroxides (e.g. hydrogen peroxide or oxone ($2KSO_5 \cdot KHSO_4 \cdot K_2SO_4$)).

General Preparation Method 6

Step (I): The optically active compound (22) can be also obtained by resolving the racemic compound (21) of the present invention using a chiral solid phase by means of HPLC.

The chiral solid phase includes cellulose esters, cellulose carbamates, amylose carbamates, crown ethers, polymethacrylates, etc.

Step (J): The racemic carboxylic acid derivative (23) can be resolved to an optically active compound (24) by forming a salt with a chiral amine.

Examples of the chiral amine are (+) or (−)-1-phenylethylamine, (+) or (−)-2-amino-1-butanol, (+) or (−)-alaninol, brucine, cinchonidine, cinchonine, kinin, quinidine and dehydroabiethylamine.

The optically active form (22) can be obtained by amidating the optically active form (24) according to Step (B).

General Preparation Method 7

In the compound (21) or (22) of the present invention shown in General Preparation Method 6, when one or both of $R^1$ and $R^2$ have nitrogen atoms protected by an acyl group or an alkoxycarbonyl group, these protective groups can be deprotected with an acid or a base to give a compound of the present invention.

Examples of the acid are trifluoroacetic acid, formic acid, hydrogen chloride, hydrogen bromide, hydrochloric acid and hydrobromic acid. Examples of the base are potassium carbonate, sodium carbonate, potassium hydroxide, sodium hydroxide, lithium hydroxide and barium hydroxide.

INDUSTRIAL APPLICABILITY

The compounds of the present invention have a high affinity for MDR, and therefore they are useful as therapeu-

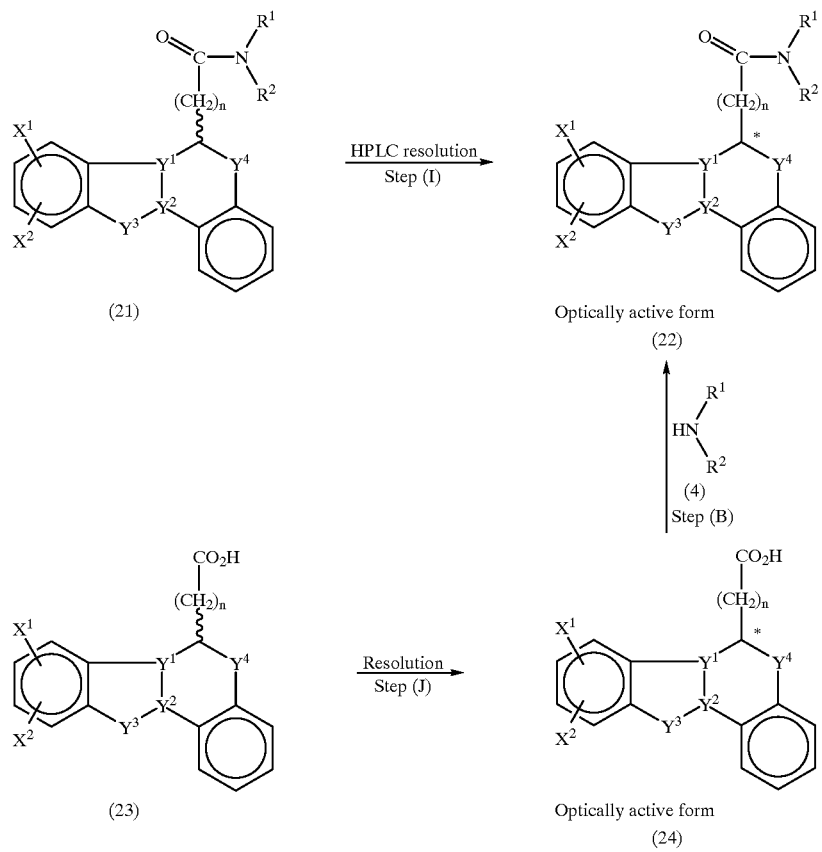

tic or preventive drugs of central diseases such as anxiety, related diseases thereto, depression, epilepsy, sleeping disorders, recognition and learning disability or schizophrenia, dyskinesia accompanied by muscle rigidity, feeding disorders, circulation disorders, drug dependence, cancer, lipid metabolism abnormality, cerebral infarction, AIDS, Alzheimer's disease or Huntington chorea.

BEST MODE OF CARRYING OUT THE INVENTION

The present invention is illustrated in more detail by showing the following examples and an experiment.

EXAMPLE 1

Preparation of N-2-(Propylamino)ethyl-N-hexyl-6,11-dihydro-5-thia-11-aza-benzo[a]fluoren-6-carboxamide (1) To a solution of 22.54 g of (4-oxo-thiochroman-2-yl) carboxylic acid and 10.7 ml of phenylhydrazine in 100 ml of ethanol was added 15 ml of sulfuric acid, followed by reflux under heating for 5 hours. The reaction solution was cooled to room temperature, poured into 500 ml of ice water and extracted with ether. The extract was washed with a saturated aqueous sodium chloride solution and dried over anhydrous sodium sulfate. After removal of the drying agent by filtration, the filtrate was concentrated under reduced pressure, and the residue was recrystallized from ethanol-hexane to give 21.85 g of ethyl 6,11-dihydro-5-thia-11-aza-benzo[a]fluoren-6-carboxylate.

(2) A solution of 19.46 g of potassium hydroxide in 40 ml of water was added to a solution of 21.63 g of ethyl 6,11-dihydro-5-thia-11-aza-benzo[a]fluoren-6-carboxylate in 100 ml of ethanol. After reflux under heating for 2 hours, the reaction solution was adjusted to pH 3 with conc. hydrochloric acid, and extracted with ethyl acetate. The extract was washed with a saturated aqueous sodium chloride solution and dried over anhydrous sodium sulfate. After removal of the drying agent by filtration, the filtrate was concentrated under reduced pressure, and the residue was recrystallized from ethanol-hexane to give 19.94 g of 6,11-dihydro-5-thia-11-aza-benzo[a]fluoren-6-carboxylic acid.

m.p. 141.5–142.5° C.

(3) To a solution of 844 mg of 6,11-dihydro-5-thia-11-aza-benzo[a]fluoren-6-carboxylic acid and 1.66 g of N-2-(N-t-butoxycarbonylpropylamino)ethyl-hexylamine in 44 ml of dichloromethane were added 552 mg of 1-hydroxybenzotriazole monohydrate and 863 mg of N-ethyl-N'-dimethylaminopropylcarbodiimide hydrochloride, followed by stirring at room temperature overnight. The reaction solution, after concentration under reduced pressure, was dissolved in ethyl acetate, washed with water 5% aqueous potassium bisulfate solution, a saturated aqueous sodium bicarbonate solution and a saturated sodium chloride solution, and dried over anhydrous sodium sulfate. After removal of the drying agent by filtration, the filtrate was concentrated under reduced pressure, and the residue was subjected to flash chromatography (silica gel; Chromatorex NHDM1020 produced by Fuji-Davison Chemical Co., developing solvent; hexane-ethyl acetate=2:1–3:2) to give 1.35 g of N-2-(N-t-butoxycarbonylpropylamino)ethyl-N-hexyl-6,11-dihydro-5-thia-11-aza-benzo[a]fluoren-6-carboxamide as an amorphous substance.

(4) In 4.3 ml of 99% formic acid was stirred 600 mg of N-2-(N-t-butoxycarbonylpropylamino)ethyl-N-hexyl-6,11-dihydro-5-thia-11-aza-benzo[a]fluoren-6-carboxamide for 5 hours. The reaction solution, after concentration under reduced pressure, was dissolved in ethyl acetate, washed with a saturated aqueous sodium bicarbonate solution and a saturated sodium chloride solution, and dried over anhydrous sodium sulfate. After removal of the drying agent by filtration, the filtrate was concentrated under reduced pressure, and the residue was recrystallized from ethyl acetate to give 406 mg of N-2-(propylamino)ethyl-N-hexyl-6,11-dihydro-5-thia-11-aza-benzo[a]fluoren-6-carboxamide.

The structures and physical property data of the present compound and the compounds prepared similarly are shown in Table 1.

EXAMPLE 2

Preparation of N,N-Dihexyl-6,11-dihydro-5-thia-11-aza-benzo[a]fluoren-6-carboxamide (1) To a solution of 20.00 g of (4-oxo-thiochroman-2-yl)-carboxylic acid in 200 ml of benzene was added 14.0 ml of thionyl chloride, followed by reflux under heating for 3 hours. The reaction solution was concentrated under reduced pressure to give a residue, a solution of which in 100 ml of dichloromethane was added dropwise to a solution of 24.6 ml of dihexylamine and 20.0 ml of triethylamine in 200 ml of dichloromethane under ice-cooling with stirring. After stirring at room temperature overnight, the reaction solution was concentrated under reduced pressure, and to the residue was added ethyl acetate, and the mixture was washed with water, 1 N hydrochloric acid, a saturated aqueous sodium bicarbonate solution and a saturated aqueous sodium chloride solution, and dried over anhydrous sodium sulfate. After removal of the drying agent by filtration, the filtrate was concentrated under reduced pressure. The residue was purified by chromatography (silica gel; Wakogel C200 (manufactured by Wako Pure Chemicals), developing solvent; hexane-ethyl acetate=5:1–3:1) and recrystallized from hexane to give 29.22 g of N,N-dihexyl-(4-oxo-thiochroman-2-yl)-carboxamide.

(2) N,N-Dihexyl-(4-oxo-thiochroman-2-yl)-carboxamide (1.00 g) and phenylhydrazine (0.26 ml) were stirred at 100° C. for 30 minutes, and the reaction mixture was dried under reduced pressure at 50° C. for 30 minutes. The residue, after addition of 1.44 g of anhydrous zinc chloride, was stirred at 170° C. for 5 minutes, and cooled to room temperature. To the reaction mixture was added ice water, followed by extracting with ethyl acetate. The extract was washed with 1N hydrochloric acid, a saturated aqueous sodium bicarbonate solution and a saturated aqueous sodium chloride solution, and dried over anhydrous sodium sulfate. After removal of the drying agent by filtration, the filtrate was concentrated under reduced pressure. The residue was recrystallized from ethyl acetate-hexane to give 0.79 g of N,N-dihexyl-6,11-dihydro-5-thia-11-aza-benzo[a]fluoren-6-carboxamide.

(3) Racemic N,N-dihexyl-6,11-dihydro-5-thia-11-aza-benzo[a]fluoren-6-carboxamide was resolved by high performance liquid chromatography (Chiralpak AD (manufactured by Daicel Co.), 2Φ×25 cm, mobile phase: hexane-ethanol=3:7, flow rate: 5 ml/min).

(−)-N,N-Dihexyl-6,11-dihydro-5-thia-11-aza-benzo[a]fluoren-6-carboxamide $[\alpha]_D^{26}$ −25.9 (c=0.180, EtOH), retention time: 20 min.

(+)-N,N-Dihexyl-6,11-dihydro-5-thia-11-aza-benzo[a]fluoren-6-carboxamide

[α]$_D^{26}$ +25.9 (c=0.207, EtOH), retention time: 37 min.

The structure and physical property data of the present compound and the compounds prepared similarly are shown in Tables 1 and 2.

EXAMPLE 3

Preparation of N,N-Dihexyl-6,11-dihydro-11-methyl-5-thia-11-aza-benzo[a]fluoren-6-carboxamide To a solution of 200 mg of N,N-dihexyl-6,11-dihydro-5-thia-11-aza-benzo[a]fluoren-6-carboxamide in 10 ml of N,N-dimethylformamide was added 21 mg of 60% sodium hydride/oil, followed by stirring at room temperature for an hour. To the solution was added 33 μl of methyl iodide, followed by stirring at room temperature for 5 hours. The reaction solution, after addition of ethyl acetate, was washed with water, 1 N hydrochloric acid, a saturated aqueous sodium bicarbonate solution and a saturated aqueous sodium chloride solution, and dried over anhydrous sodium sulfate. After removal of the drying agent by filtration, the filtrate was concentrated under reduced pressure. The residue was recrystallized from hexane to give 155 mg of N,N-dihexyl-6,11-dihydro-11-methyl-5-thia-11-aza-benzo[a]fluoren-6-carboxamide.

The structures and physical property data of the present compound and the compounds prepared similarly are shown in Table 2.

EXAMPLE 4

Preparation of N,N-Dihexyl-5,6-dihyro-benzo[4,5]imidazo[2,1-a]isoquinoline-6-carboxamide (1) To a solution of 0.49 g of sodium in 20 ml of ethanol was added dropwise a solution of 5.90 g of diethyl 2-N-t-butoxycarbonylaminomalonate in 10 ml of ethanol with stirring at room temperature. After stirring for 20 minutes, to the reaction solution was added a solution of 4.00 g of 2-cyanobenzyl bromide in 10 ml of ethanol, and the mixture was stirred at room temperature for 10 minutes and then at heating reflux for 3.5 hours. The reaction solution was concentrated under reduced pressure, and the residue, after addition of ethyl acetate, was washed with water, 5% aqueous potassium bisulfate solution, a saturated aqueous sodium bicarbonate solution and a saturated sodium chloride solution, and dried over anhydrous sodium sulfate. After removal of the drying agent by filtration, the filtrate was concentrated under reduced pressure, and the residue was purified by chromatography (silica gel; Wakogel C200 (manufactured by Wako Pure Chemicals), developing solvent; hexane-ethyl acetate=5:1) to give 7.86 g of diethyl 2-(2-cyanobenzyl)-2-N-t-butoxycarbonylaminomalonate as an oil.

(2) To 1.17 g of diethyl 2-(2-cyanobenzyl)-2-N-t-butoxycarbonylaminomalonate were added 20 ml of ethanol and an aqueous sodium hydroxide solution (0.36 g of sodium hydroxide/0.5 ml of water), followed by stirring while heating under reflux for 2 hours. The reaction solution was concentrated under reduced pressure, and to the residue was added 5% aqueous potassium bisulfate solution, followed by extracting with ethyl acetate. The extract was washed with a saturated sodium chloride solution, and dried over anhydrous sodium sulfate. After removal of the drying agent by filtration, the filtrate was concentrated under reduced pressure to give 0.81 g of a crude N-t-butoxycarbonyl-(2-cyanophenyl)alanine as an oil, which was then used for the next step without purification.

(3) To a solution of 0.81 g of the crude N-t-butoxycarbonyl-(2-cyanophenyl)alanine and 0.67 g of dihexylamine in 8 ml of N,N-dimethylformamide were added 0.55 g of 1-hydroxybenzotriazole monohydrate and 0.69 g of N-ethyl-N'-dimethylaminopropylcarbodiimide hydrochloride, followed by stirring at room temperature overnight. The reaction mixture was poured into water and extracted with ethyl acetate. The extract was washed with 5% aqueous potassium bisulfate solution, a saturated aqueous sodium bicarbonate solution and a saturated sodium chloride solution, and dried over anhydrous sodium sulfate. After removal of the drying agent by filtration, the filtrate was concentrated under reduced pressure. The residue was purified by chromatography (silica gel; Wakogel C200 (manufactured by Wako Pure Chemicals), developing solvent; hexane-ethyl acetate=4:1) to give 1.01 g of N-t-butoxycarbonyl-(2-cyanophenyl)alanine dihexylamide.

(4) To a solution of 0.98 g of N-t-butoxycarbonyl-(2-cyanophenyl)alanine dihexylamide in 1.7 ml of dichloromethane was added 1.7 ml of trifluoroacetic acid, followed by stirring at room temperature for 1.5 hours. The reaction solution was concentrated under reduced pressure, and to the residue was added an aqueous sodium bicarbonate solution, followed by extracting with dichloromethane. The extract was washed with a saturated sodium chloride solution, and dried over anhydrous sodium sulfate. After removal of the drying agent by filtration, the filtrate was concentrated under reduced pressure to give 0.76 g of a crude (2-cyanophenyl)alanine dihexylamide, which was then used for the next step without purification.

(5) The crude (2-cyanophenyl)alanine dihexylamide (0.76 g), 2-fluoronitrobenzene (0.30 g) and anhydrous potassium carbonate (0.36 g) in 8 ml of N,N-dimethylformamide were refluxed under heating for 2.5 hours. The reaction mixture was poured into water and extracted with ethyl acetate. The extract was water and a saturated sodium chloride solution, and dried over anhydrous sodium sulfate. After removal of the drying agent by filtration, the filtrate was concentrated under reduced pressure, and the residue was purified by chromatography (silica gel; Wakogel C200 (manufactured by Wako Pure Chemicals), developing solvent; hexane-ethyl acetate=5:1) to give 0.42 g of N-(2-nitrophenyl)-(2-cyanophenyl)alanine dihexylamide.

(6) N-(2-Nitrophenyl)-(2-cyanophenyl)alanine dihexylamide (95 mg) and platinum dioxide (10 mg) in 3 ml of methanol were stirred under a hydrogen atmosphere for 2 hours. The insoluble matter was removed by filtration using a Celite plate, and the filtrate was concentrated under reduced pressure.

The residue was dissolved in 5 ml of ethanol, and hydrogen chloride gas was blown to give a saturated solution. The reaction solution, after stirring for 4 hours, was poured into an aqueous sodium bicarbonate solution, followed by extracting with ethyl acetate. The extract was washed with a saturated sodium chloride solution, and dried over anhydrous sodium sulfate. After removal of the drying agent by filtration, the filtrate was concentrated under reduced pressure. The residue was purified by chromatography (silica gel; Wakogel C200 (manufactured by Wako Pure Chemicals), developing solvent; hexane-ethyl acetate=2:1) and recrystallized from ethyl acetate to give 24 mg of N,N-dihexyl-5,6-dihydro-benzo[4,5]imidazo[2,1-a]isoquinoline-6-carboxamide.

The structures and physical property data of the present compound and the compounds prepared similarly are shown in Table 3.

EXAMPLE 5

Preparation of N,N-Dipropyl-6,11-dihyro-5-thia-11-aza-benzo[a]fluoren-6-carboxamide 5,5-Dioxide To a solution of 500 mg of N,N-dipropyl-6,11-dihydro-5-thia-11-aza-benzo[a]fluoren-6-carboxamide in 30 ml of dichloromethane was added dropwise a solution of 710 mg of m-chloroperbenzoic acid (containing 70% or more) in 30 ml of dichloromethane under ice-cooling with stirring over 20 minutes. After further stirring at room temperature for an hour, the reaction mixture was concentrated under reduced pressure, and the residue was dissolved in ethyl acetate, washed with a saturated aqueous sodium bicarbonate solution and a saturated sodium chloride solution, and dried over anhydrous sodium sulfate. After removal of the drying agent by filtration, the filtrate was concentrated under reduced pressure. The residue was purified by chromatography (silica gel; Wakogel C200 (manufactured by Wako Pure Chemicals), developing solvent; hexane-ethyl acetate= 3:1–1:1) and recrystallized from ethyl acetate-hexane to give 230 mg of N,N-dipropyl-6,11-dihydro-5-thia-11-aza-benzo[a]fluoren-6-carboxamide 5,5-dioxide.

The structures and physical property data of the present compound and the compounds prepared similarly are shown in Table 2.

TABLE 1

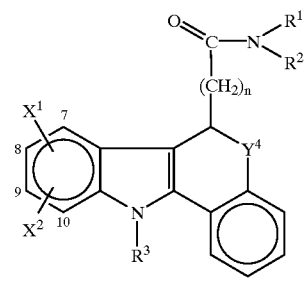

| Comp. No.[1] | Exp. No.[2] | $R^1$ | $R^2$ | n | $X^1$ | $X^2$ | $R^3$ | $Y^4$ | m.p. (Recry. sol.[3]) (° C.) |
|---|---|---|---|---|---|---|---|---|---|
| 01 | 2 | H | H | 0 | H | H | H | S | 241.0~242.5 (AcOEt) |
| 02 | 2 | n-Pr | H | 0 | H | H | H | S | 172.0~174.0 (AcOEt/Hex) |
| 03 | 2 | Me | Me | 0 | H | H | H | S | 254.5~256.5 (AcOEt) |
| 04 | 2 | Et | Et | 0 | H | H | H | S | 242.0~243.5 (AcOEt) |
| 05 | 2 | n-Pr | n-Pr | 0 | H | H | H | S | 196.0~197.0 (AcOEt) |
| 06 | 2 | n-Hex | n-Hex | 0 | H | H | H | S | 138.5~140.0 (AcOEt/Hex) |
| 07[4] | 2 | n-Hex | n-Hex | 0 | H | H | H | S | 99.0~100.5 (Standing[5]) |
| 08[4] | 2 | n-Hex | n-Hex | 0 | H | H | H | S | 98.0~99.0 (Standing[5]) |
| 09 | 2 | n-Hex | n-Hex | 0 | 8-F | H | H | S | 110.5~112.5 (AcOEt/Hex) |
| 10 | 2 | n-Hex | n-Hex | 0 | 8-Cl | H | H | S | 123.0~124.5 (AcOEt/Hex) |
| 11 | 2 | n-Hex | n-Hex | 0 | 8-Me | H | H | S | 139.5~141.5 (AcOEt/Hex) |
| 12 | 2 | n-Hex | n-Hex | 0 | 8-F | 10-F | H | S | 148.0~149.0 (AcOEt/Hex) |
| 13 | 1 | n-Hex | $CH_3(CH_2)_2NH(CH_2)_2$ | 0 | H | H | H | S | 135.5~138.0 (AcOEt) |
| 14 | 1 | n-Hex | $CH_3(CH_2)_2O(CH_2)_2$ | 0 | H | H | H | S | 165.0~167.0 (AcOEt) |
| 15 | 2 | $CH_3O(CH_2)_2$ | $CH_3O(CH_2)_2$ | 0 | H | H | H | S | 206.0~208.0 (AcOEt) |

[1]Compound number
[2]Example number used for synthesis of the compound.
[3]Recrystallization solvent: AcOEt = ethyl acetate, Hex = hexane, $Et_2O$ = diethyl ether.
[4]Optically active forms of Compound 6: Compound 7 = (−)-Compound 6, Compound 8 = (+)-Compound 6.
[5]Crystallization by a column purification, drying and standing.
In $R^1$ and $R^2$, n-Hex is an n-hexyl group and n-Pr is an n-propyl group.

TABLE 2

| Comp. No.[1] | Exp. No.[2] | R$^1$ | R$^2$ | n | X$^1$ | X$^2$ | R$^3$ | Y$^4$ | m.p. (°C.) | (Recry. sol. [3]) |
|---|---|---|---|---|---|---|---|---|---|---|
| 16 | 3 | n-Hex | n-Hex | 0 | H | H | Me | S | 111.0~112.0 | (Hex) |
| 17 | 3 | n-Hex | n-Hex | 0 | H | H | (CH$_3$)$_2$N(CH$_2$)$_4$ | S | 50.0~52.0 | (Hex) |
| 18 | 3 | n-Hex | n-Hex | 0 | H | H | (CH$_3$)$_2$N(CH$_2$)$_2$ | S | 89.5~90.5 | (Et$_2$O/Hex)[4] |
| 19 | 2 | n-Hex | n-Hex | 1 | H | H | H | S | 155.0~157.0 | (AcOEt/Hex) |
| 20 | 5 | n-Pr | H | 0 | H | H | H | SO$_2$ | 296.5~298.0 | (AcOEt) |
| 21 | 5 | n-Pr | n-Pr | 0 | H | H | H | SO$_2$ | 266.0~267.0 | (AcOEt/Hex) |
| 22 | 5 | n-Hex | n-Hex | 0 | H | H | H | SO$_2$ | 156.0~157.0 | (AcOEt/Hex) |
| 23 | 2 | n-Hex | n-Hex | 0 | H | H | H | CH$_2$ | 152.0~153.5 | (AcOEt/Hex) |
| 27 | 2 | n-Hex | n-Hex | 0 | H | H | H | OHCN | 137.0~139.0 | (Et$_2$O/Hex) |
| 28 | 2 | n-Hex | n-Hex | 0 | H | H | H | AcN | 145.0~146.0 | (AcOEt/Hex) |

[1]Compound number
[2]Example number used for synthesis of the compound.
[3]Recrystallization solvent: AcOEt = ethyl acetate, Hex = hexane, Et$_2$O = diethyl ether.
[4]Monohydrochloride
In R$^1$ and R$^2$, n-Hex is an n-hexyl group and n-Pr is an n-propyl group.

TABLE 3

| Comp. No.[1] | Exp. No.[2] | R$^1$ | R$^2$ | n | X$^1$ | X$^2$ | Y$^4$ | m.p. (°C.) | (Recry. sol.[3]) |
|---|---|---|---|---|---|---|---|---|---|
| 24 | 4 | n-Et | n-Et | 0 | H | H | CH$_2$ | 206.5~207.5 | (Standing[4]) |
| 25 | 4 | n-Pr | n-Pr | 0 | H | H | CH$_2$ | 188.5~190.0 | (AcOEt/Hex) |
| 26 | 4 | n-Hex | n-Hex | 0 | H | H | CH$_2$ | 134.5~136.5 | (AcOEt) |

[1]Compound number
[2]Example number used for synthesis of the compound.
[3]Recrystallization Solvent: AcOEt = ethyl acetate, Hex = hexane.
[4]Crystallization by a column purification, drying and standing.
In R$^1$ and R$^2$, n-Hex is an n-hexyl group and n-Pr is an n-propyl group.

Experiment [MDR Receptor Binding Assay]

Crude mitochondria fractions prepared from rat cerebral cortex were used as a receptor sample, and [$^3$H]PK11195 was used as a [$^3$H]-labeled ligand.

A binding assay using the [$^3$H]-labeled ligand was carried out according to the following method as described in Journal of Pharmacology and Experimental Therapeutics, 262, 971(1992).

Preparation of Receptor Sample: Rat cerebral cortex was homogenized using a Teflon-coated homogenizer in a 10 mM HEPES buffer (pH 7.4) containing 0.32 M sucrose in ten volumes of the wet weight. The homogenate was centrifuged at 900× g for 10 minutes, and the resulting supernatant was centrifuged at 9,000× g for 10 minutes. The precipitate was suspended in a HEPES buffer to give a protein concentration of 1 mg/ml, and centrifuged at 12,000× g for 10 minutes. The resulting precipitate was suspended in a 50 mM HEPES buffer (pH 7.4) to give a crude mitochondria fraction.

MDR Binding Assay: Mitochondria sample (1.0 mg protein/ml), [$^3$H]PK11195 (2 nM) and the test drug were reacted at 4° C. for 90 minutes.

After completion of the reaction, the reaction mixture was filtered with suction through a glass filter (GF/B) treated with 0.3% polyethyleneimine, and the radioactivity on the filter was measured by a liquid scintillation spectrometer.

The binding at the reaction in the presence of 10 μM PK11195 was defined as non-specific binding of [$^3$H] PK11195, and the difference between total binding and non-specific binding was defined as specific binding. A fixed concentration of [$^3$H]PK11195 (2 nM) was reacted with varied concentrations of the test drug under the above-mentioned conditions to give an inhibition curve, and the concentration (IC$_{50}$) of the test drug to exhibit 50% inhibition of [$^3$H]PK11195 binding was measured by the inhibition curve, and results are shown in Table 4.

TABLE 4

| Compound No. | MDR IC$_{50}$(nM) |
|---|---|
| 02 | 55.9 |
| 03 | 38.5 |
| 04 | 0.443 |
| 05 | 0.368 |
| 06 | 3.76 |
| 07 | 42.3 |
| 08 | 2.15 |
| 09 | 13.8 |
| 10 | 20.1 |
| 11 | 13.9 |
| 12 | 22.1 |
| 14 | 1.35 |
| 15 | 4.98 |
| 16 | 1.35 |
| 21 | 1.12 |
| 22 | 1.23 |
| 23 | 1.35 |
| 25 | 73.9 |

TABLE 4-continued

| Compound No. | MDR IC$_{50}$(nM) |
|---|---|
| 26 | 42.3 |
| 27 | 35.1 |
| 28 | 12.6 |

What is claimed is:

1. A nitrogen-containing tetracyclic compound represented by the formula:

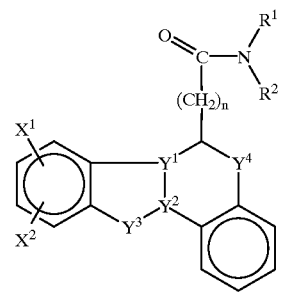

wherein $Y^1$—$Y^2$—$Y^3$ is N—C=N or a group represented by the formula: C=C—NR$^3$ (wherein R$^3$ is a hydrogen atom, a C$_{1-5}$ alkyl group or a nitrogen-containing C$_{2-10}$ alkyl group), Y$^4$ is S, SO, SO$_2$, CH$_2$ or a group represented by the formula: NR$^4$ (wherein R$^4$ is a C$_{1-5}$ alkanoyl group or a C$_{1-5}$ alkyl group), R$^1$ and R$^2$ are the same or different, and are each a hydrogen atom, a C$_{1-10}$ alkyl group, a C$_{3-15}$ alkoxyalkyl group or a C$_{3-15}$ alkylaminoalkyl group, or R$^1$ and R$^2$ taken together with the nitrogen atom to which they are attached form a cyclic amino group, X$^1$ and X$^2$ are the same or different, and are each a hydrogen atom, a C$_{1-5}$ alkyl group, a C$_{1-5}$ alkoxy group or a halogen atom, and n is 0, 1 or 2; or a pharmaceutically acceptable salt thereof.

* * * * *